United States Patent
Chou et al.

(10) Patent No.: US 6,313,293 B1
(45) Date of Patent: Nov. 6, 2001

(54) PREPARATION OF AMIDES AND QUINAZOLINE DERIVATIVES

(75) Inventors: Wen-Chih Chou; Ming-Chen Chou; Yann-Yu Lu; Shyh-Fong Chen, all of Taipei (TW)

(73) Assignee: Development Center for Biotechnology, Taipei (TW)

( * ) Notice: Subject to any disclaimer, the term of this patent is extended or adjusted under 35 U.S.C. 154(b) by 0 days.

(21) Appl. No.: 09/516,960

(22) Filed: Mar. 1, 2000

(30) Foreign Application Priority Data

Mar. 29, 1999 (TW) .................................. 88104933

(51) Int. Cl.[7] .......................... C07F 7/10; C07D 401/02; C07D 405/02
(52) U.S. Cl. .......................... 544/283; 544/374; 544/377; 544/386; 549/487; 556/410; 556/412
(58) Field of Search .................. 544/374, 377, 544/386, 487, 284; 564/133–144; 556/410, 412

(56) References Cited

FOREIGN PATENT DOCUMENTS 28 47 623 * 5/1979 (DE) .

OTHER PUBLICATIONS

CASREACT printout for Rigo et al, Feb. 1994.*
Campbell, Simon F., et al., "3,4–Diamino–6,7–dimethoxyquinazolines" *J. Med. Chem*, 1987, 30, 49–57.
Boschi, D. et al., "$\alpha_1$—Adrenoceptor Blocking Activity of Some Ring–open Analogues of Prazosin", *Arch. Pharm.*, 1994, 327, 661–667.
Althius, T.H. et al., "Synthesis and Identification of the Major Metabolites of Prazosin Formed in Dog and Rat", *J. Med. Chem.*, 1977, 20, 146–149.
Desai, M. et a., "A Convenient Preparation of 1–Aroylpiperazines", *Org. Prep. Proced. Int.*, 1976, 8, 85–86.
Manoury, P.M., et al., "Synthesis and Antihypertinsive Activity of a Series of 4–Amino–6,7–dimethoxyquinazoline Derivatives", *J. Med. Chem.*, 1986, 29, 19–25.
F. Novelli, et al., "Synthesis and Preliminary Pharmacological Evaluation of 3–[2–(1–Aryl–Piperazin–4–YL)Ethyl]–3, 4–Dihydro–3–Methyl–6–R–1,2,4–benzotriazines", *Farmaco*51 (8,9), 551–558 (1996).*

* cited by examiner

Primary Examiner—Mukund J. Shah
Assistant Examiner—Hong Liu
(74) *Attorney, Agent, or Firm*—Kenyon & Kenyon

(57) ABSTRACT

The present invention relates to a process for the preparation of amides, comprising reacting amines with carboxylic acids in the presence of silicon amines. The present invention further relates to a process for the preparation of quinazoline derivatives, comprising reacting amines with carboxylic acids in the presence of silicon amines to obtain amides and contacting the resultant amides with quinazoline.

20 Claims, No Drawings

PREPARATION OF AMIDES AND QUINAZOLINE DERIVATIVES

FIELD OF THE INVENTION

The invention relates to a process for the preparation of amides, comprising reacting amines with carboxylic acids in the presence of silicon amines. The resulting amides are useful as the precursors of anti-hypertension medicines.

BACKGROUND OF THE INVENTION

An amide unit is a very common functional group and exhibits major features in several important natural products or artificial compounds. A number of compounds with the structure of an amide display a very important character in the synthesis of medicines. For example, these compounds are useful as intermediates or precursors in the synthesis of final medicines. For example, the N-acylalkylenediamines of formula (I') or (II') are amides and can be respectively used as the intermediates for the synthesis of the anti-hypertension medicines of formula (I) or (II).

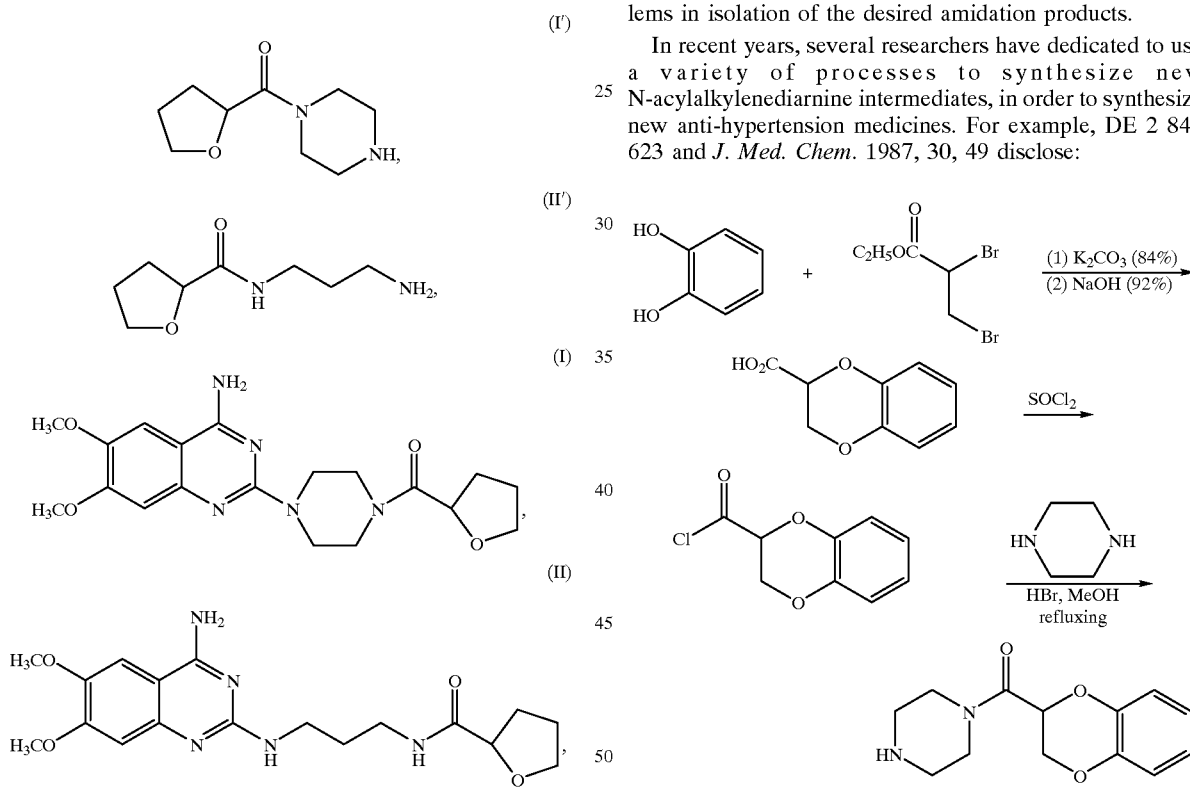

Generally speaking, the synthesis of such type of anti-hypertension medicines is conducted by reacting the quinazolinyl chloride intermediate of formula (III) with the N-acylalkylenediarnine intermediate of formula (I') or (II'), to obtain a compound of formula (I) or (II).

As to the synthesis of the intermediate of formula (III), i.e. 4-amino-2-chloro-6,7-dimethoxyquinazoline, DE 2 847 623 and *J. Med. Chem.* 1987, 30, 49 have fully disclosed the synthesis procedures.

There are a number of known methods for the synthesis of amides. For example, they can be produced by the reaction of amines with esters, which involves known, basic organic chemical reactions. Under heating conditions, the reaction of a primary amine and an ester can directly produce an amide bond. However, such a reaction mostly needs to be conducted in the presence of solvents. As to the amidation reaction of a secondary amine and an ester, it needs to be conducted under the catalysis of Lewis acids, strong bases or enzymes, in addition to the presence of solvents.

The conventional methods for direct conversion of carboxylic acids to amides require either a very high reaction temperature (over 190° C.) or special coupling agents, such as carbodumides, phosphorus agents and uronium salts. These coupling agents require preparation and cause problems in isolation of the desired amidation products.

In recent years, several researchers have dedicated to use a variety of processes to synthesize new N-acylalkylenediarnine intermediates, in order to synthesize new anti-hypertension medicines. For example, DE 2 847 623 and *J. Med. Chem.* 1987, 30, 49 disclose:

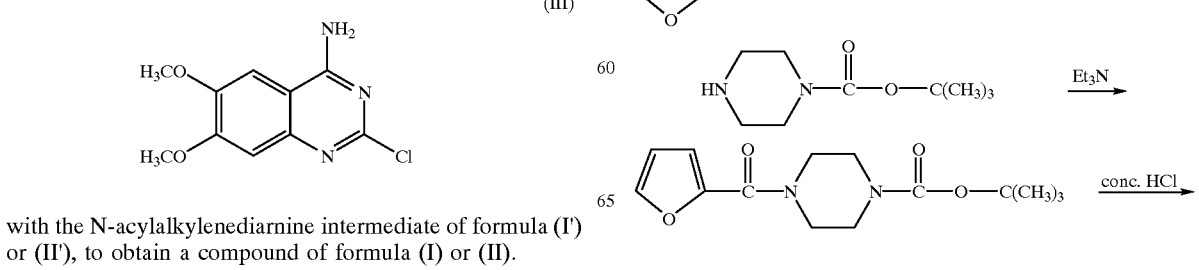

*Arch. Pharm.* 1994, 327, 661 discloses:

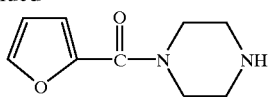

*Farmaco.* 1996, 51, 551, *J. Med. Chem.* 1977, 20, 146 and U.S. Pat. No. 4,026,894 disclose:

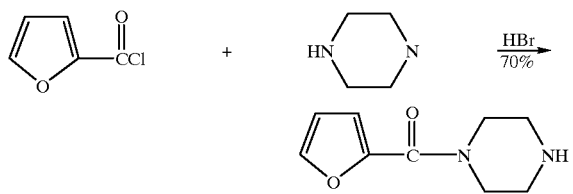

*Org. Prep. Proced. Int.* 1976, 8, 85 discloses:

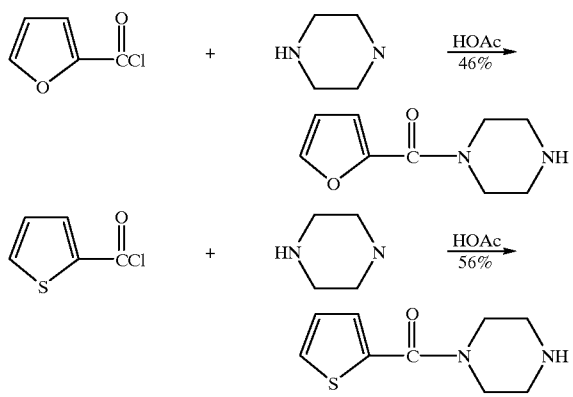

*J. Med. Chem.* 1986, 29, 19 discloses:

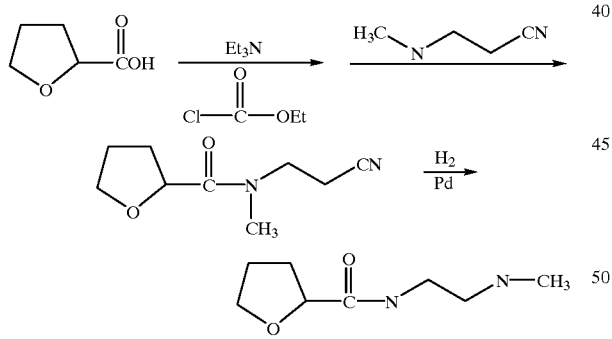

U.S. Pat. No. 4,093,726 discloses:

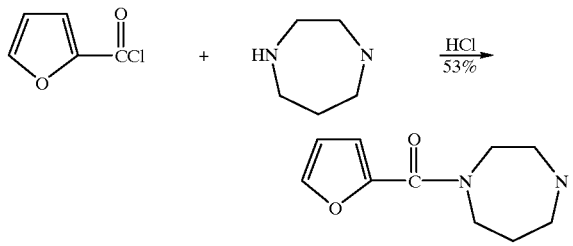

In view of the above, conventional processes for the preparation of N-acylalkylenediamine intermediates have the following characteristics:

(1) The processes use the corresponding organic acids as starting materials, activate the starting materials to form acyl chlorides or higher active intermediates such as anhydrides, then react the acyl chlorides or anhydrides with diamines to obtain the desired N-acylalkylenediamines. The reaction procedures of these processes are too complicated and the Yield: is low (about 40%–70%). Also, these processes may produce waste chemicals causing environmental problems.

(2) Since the reactivity of acyl chlorides or anhydrides is very high, one of the amino groups in the diamines used needs to be protected by hydrogen chloride, hydrogen bromide, acetic acid or a tertiary butyloxycarbonyl compound to prevent diamides formation. Subsequently, the deprotection step is required to obtain the desired N-acylalkylenediamines.

Therefore, the object of the present invention is to provide a process for the preparation of amides with simple steps and high Yield:, which simply reacts amines and carboxylic acids in the presence of silicon amines to form amides in situ. The process of the invention does not require the conversion of acids to alkyl esters, neither does it require high reaction temperatures or additional agents.

SUMMARY OF THE INVENTION

The present invention relates to a process for the preparation of amides, which comprises reacting amines with carboxylic acids in the presence of silicon amines.

This invention further relates to a process for the preparation of quinazoline derivatives, which comprises reacting amines with carboxylic acids in the presence of silicon amines to obtain amides, and contacting the resulting amides with a quinazoline.

DETAILED DESCRIPTION OF THE INVENTION

The present invention first relates to a process for the preparation of amides, which comprises reacting amines with carboxylic acids in the presence of silicon amines.

The amines suitable for the process for the preparation of amides of the present invention comprise the amines of the following formulae:

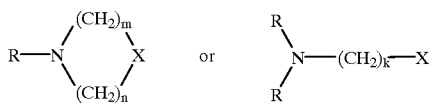

wherein R is the same or different and selected from hydrogen, $C_{1-6}$ alkyl, and $C_{2-6}$ alkenyl; preferably selected from hydrogen and $C_{1-6}$ alkyl; most preferably selected from hydrogen and methyl; X is CR or NR, R is as defined above; m is 2 or 3, preferably 2; n is 2 or 3, preferably 2; k is 1 to 8; preferably 3.

The carboxylic acids suitable for the process for the preparation of amides of the present invention comprise the carboxylic acids of the following formula:

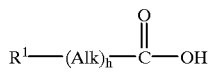

wherein $R^1$ is selected from hydrogen, $C_{1-6}$ alkyl, $C_{1-6}$ alkoxy, $C_{2-6}$ alkenyl, aryl, heterocyclyl, and

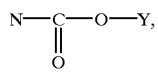

wherein Y is selected from hydrogen, $C_{1-6}$ alkyl, and $C_{2-6}$ alkenyl; $R^1$ is preferably selected from $C_{1-6}$ alkyl, phenyl, 4 to 7 membered heterocyclyl which contains 1 to 3 the same or different hetero atoms selected from nitrogen, oxygen and sulfur, and optionally fused with phenyl or heterocyclyl, and

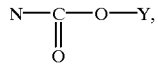

wherein Y is straight or branch $C_{1-6}$ alkyl; Alk is unsubstituted or substituted alkylene, preferably unsubstituted, hydroxyl-substituted or methyl-substituted alkylene; h is 0 to 4, preferably 0 to 2.

The silicon amines suitable for the process for the preparation of amides of the present invention comprise the silicon amines of the following formula:

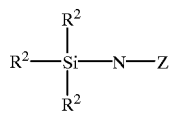

wherein $R^2$ is the same or different and selected from hydrogen, $C_{1-6}$ alkyl, and $C_{2-6}$ alkenyl, preferably unsubstituted $C_{1-6}$ alkyl; Z is selected from hydrogen, $C_{1-6}$ alkyl, $C_{2-6}$ alkenyl, and silyl, preferably $C_{1-6}$ alkyl-substituted silyl. Most preferably, the silicon amine is 1,1,1,3,3,3-hexamethyldisilazane, abbreviated as HMDS.

The present invention further relates to a process for the preparation of quinazoline derivatives, comprising reacting amines with carboxylic acids in the presence of silicon amines to obtain amides, and contacting the resulting amides with a quinazoline of the following formula:

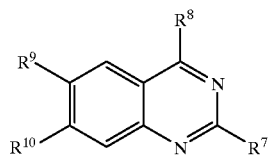

wherein $R^7$, $R_8$, $R^9$ and $R^{10}$ are independently selected from halogen, hydrogen, amino, $C_{1-8}$ alkyl, $C_{2-8}$ alkenyl, $C_{3-8}$ cycloalkyl, $C_{3-8}$ cycloalkenyl, $C_{6-12}$ aryl, $C_{1-8}$ alkoxy, $C_{1-8}$ alkylthio and $C_{3-8}$ heterocyclyl.

The amines suitable for the process for the preparation of quinazoline derivatives of the present invention comprise the amines of the following formulae:

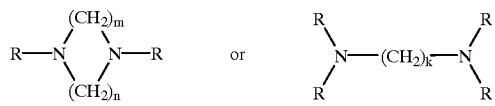

wherein R is the same or different and selected from hydrogen, $C_{1-6}$ alkyl, and $C_{2-6}$ alkenyl; preferably selected from hydrogen and $C_{1-6}$ alkyl; most preferably selected from hydrogen and methyl; X is CR or NR, R is as defined above; m is 2 or 3, preferably 2; n is 2 or 3, preferably 2; k is 1 to 8; preferably 3.

The carboxylic acids suitable for the process for the preparation of quinazoline derivatives of the present invention comprise the carboxylic acids of the following formula:

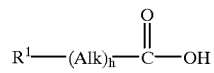

wherein $R^1$ is selected from hydrogen, $C_{1-6}$ alkyl, $C_{1-6}$ alkoxy, $C_{2-6}$ alkenyl, aryl, heterocyclyl, and

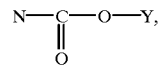

wherein Y is selected from hydrogen, $C_{1-6}$ alkyl and $C_{2-6}$ alkenyl; $R^1$ is preferably selected from $C_{1-6}$ alkyl, phenyl, 4 to 7 membered heterocyclyl which contains 1 to 3 the same or different hetero atoms selected from nitrogen, oxygen and sulfur, and optionally fused with phenyl or heterocyclyl, and

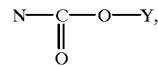

wherein Y is straight or branch $C_{1-6}$ alkyl; Alk is unsubstituted or substituted alkylene, preferably unsubstituted, hydroxyl-substituted or methyl-substituted alkylene; h is 0 to 4, preferably 0 to 2.

The silicon amines suitable for the process for the preparation of quinazoline derivatives of the present invention comprise the silicon amines of the following formula:

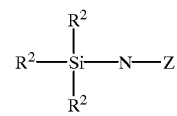

wherein $R^2$ is the same or different and selected from hydrogen, $C_{1-6}$ alkyl, and $C_{2-6}$ alkenyl, preferably unsubstituted $C_{1-6}$ alkyl; Z is selected from hydrogen, $C_{1-6}$ alkyl, $C_{2-6}$ alkenyl, and silyl, preferably $C_{1-6}$ alkyl-substituted silyl. Most preferably, the silicon amine is 1,1,1,3,3,3-hexamethyldisilazane, abbreviated as HMDS.

The term "$C_{1-6}$ alkyl" represents straight or branch alkyl having 1 to 6 carbon atoms, for example, methyl, ethyl, propyl, iso-propyl, butyl, iso-butyl, sec-butyl, tert-butyl, pentyl, iso-pentyl, tert-pentyl, and hexyl. The term "$C_{2-6}$ alkenyl" represents straight or branch alkenyl having 2 to 6 carbon atoms and having at least one double bond in any position, for example, vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl. The term "aryl" represents aromatic mono- or poly-cyclohydrocarbyl, for example, phenyl and naphthyl. The term "heterocyclyl" represents saturated, partially saturated, or unsaturated heterocyclyl, in which, in addition to carbon atoms, the ring additionally contains hetero atoms selected from oxygen, sulfur and nitrogen. The term "alkylene" represents substituent —$CH_2$—. The term "silyl" represents substituent —$SiH_3$. $C_{1-6}$ alkyl, $C_{2-6}$ alkenyl, aryl, heterocyclyl, alkylene, and silyl can be substituted with one or more substitutents such as $C_{1-6}$ alkyl and hydroxyl.

The amidation reactions of the present invention comprise adding silicon amines into the mixtures of amines and carboxylic acids in the present of nitrogen air under moderate temperatures (between 70–200° C., preferably 75–150° C.); stirring the mixtures for several hours till the amidation reactions complete; after cooling, distributing the mixtures in a proper solvent, such as the aqueous solution of chloroform and sodium hydrogen carbonate; washing the organic layer, for example, with water; drying, for example, with anhydrous sodium sulfate; and carrying to chromatography, to obtain the desired amide products. The Yield: is between 72–93%.

The feasibility of the present invention is illustrated by the following examples which are provided for illustration but not for limitation of the scope of the invention.

WORKING EXAMPLES

Example 1

The preparation of N-(tetrahydrofuran-2-carbonyl) piperazine (Compound 3)

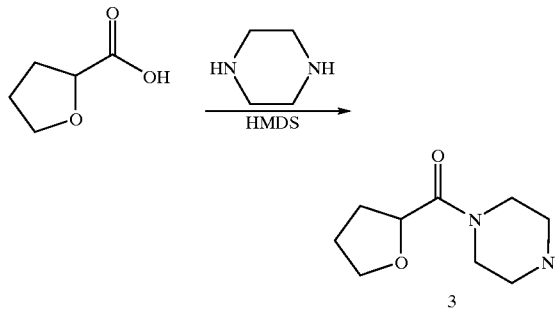

In a 100 ml round-bottom flask, tetrahydrofuran-2-carboxylic acid (3.48 grams, 30 mmole), piperazine (5.16 grams, 60 mmole) and 1,1,1,3,3,3-hexamethyldisilazane (4.83 grams, 30 mmole) were added, stirred under a nitrogen atmosphere and heated to 110° C. After 5 hours, the completion of the reaction was detected by thin-layer chromatography (TLC). After cooling to room temperature, the product was dissolved in chloroform, washed with a sodium hydrogen carbonate solution once and with water once. The organic layer was dried with anhydrous sodium sulfate, filtered, and applied suction to obtain 5.13 grams of Compound 3.

Yield:: 93%.

Compound 3: $^1$H NMR (CDCl$_3$) δ 1.87–1.91 (m, 1 H), 1.93–2.07 (m, 2 H), 2.22–2.27 (m, 1 H), 2.45 (s, 1 H, NH), 2.85–2.91 (m4 H), 3.48–3.57 (m, 2 H), 3.60–3.69 (m, 2 H), 3.86–3.90 (m, 1 H), 3.93–3.99 (m, 1 H), 4.61 (dd, J=7.3, 5.4 Hz, 1 H); $^{13}$C NMR (CDCl$_3$) δ 25.6 (t), 28.4 (t), 43.0 (t), 45.8 (t), 46.2 (t), 46.6 (t), 68.9 (t), 75.6 (d), 169.8 (s)

Example 2

The preparation of N-(1,4-benzodioxane-2-carbonyl) pierazine (Compound 4)

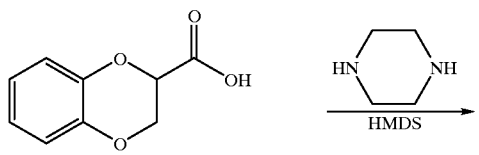

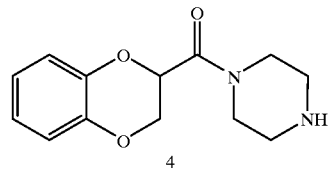

The procedures of Example 1 were followed except that 1,4-benzodioxane-2-carboxylic acid (3.6 grams, 20 mmole), piperazine (3.44 grams, 40 mmole) and 1,1,1,3,3,3-hexamethyldisilazane (6.44 grams, 40 mmole) were reacted for 5 hours under 110° C. After extraction purification, 4.51 grams of Compound 4 was obtained. Yield: 91%.

Compound 4: $^1$H NMR (CDCl$_3$) δ 2.20 (s, 1 H, NH), 2.90–2.95 (m,.2 H), 2.95–3.00 (m, 2 H), 3.56–3.61 (m, 2 H), 3.75–3.82 (m, 2 H), 4.37 (dd, J=11.9, 8.2 Hz, 1 H), 4.53 (dd, J=11.9, 2.5 Hz, 1 H), 4.87 (dd, J=8.2, 2.5 Hz, 1 H), 6.88–6.96 (m, 4 H); $^{13}$C NMR (CDCl$_3$) δ 43.2 (t), 45.8 (t), 46.4 (t), 47.0 (t), 65.2 (t), 70.5 (d), 117.3 (d), 117.4 (d), 121.5 (d), 122.2 (d), 142.6 (s), 143.3 (s), 164.8 (s)

Example 3

The preparation of N-(furan-2-carbonyl) piperazine (Compound 5)

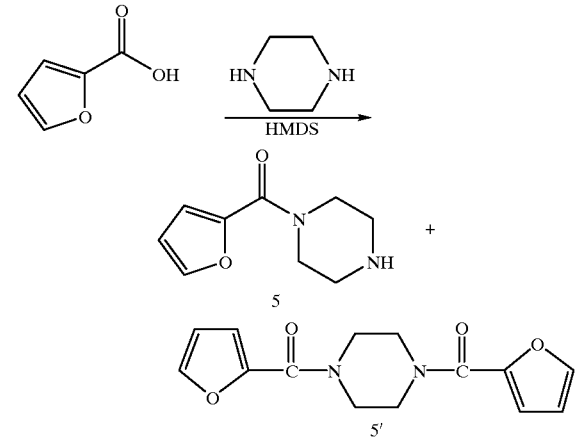

In a 100 ml round-bottom flask, furan-2-carboxylic acid (3.9 grams, 35 mmole), piperazine (6.02 grams, 70 mmole) and 1,1,1,3,3,3-hexamethyldisilazane (11.27 grams, 70 mmole) were added, stirred under a nitrogen atmosphere and heated to 110° C. After 3 hours, the completion of the reaction was detected by thin-layer chromatography (TLC). After cooling to room temperature, the product was dissolved in dichloromethane, extracted with a 0.5 N hydrochloric acid solution to form an organic layer and an aqueous layer. The organic layer was washed with a sodium hydrogen carbonate solution once and with water once, dried with anhydrous sodium sulfate, filtered, and applied suction to obtain 0.48 grams of diamide (Compound 5'). The aqueous layer was alkalified with a potassium carbonate solution to pH 10 and extracted with chloroform. The extract was dried with anhydrous sodium sulfate, filtered and applied suction to obtain 5.3 grams of Compound 5. Yield: 83%.

Compound 5: $^1$H NMR (CDCl$_3$) δ 2.27 (br s, 1 H, NH), 2.92–2.96 (m, 4 H), 3.79 (br s, 4 H), 6.49 (dd, J=3.5, 1.8 Hz, 1 H), 7.00 (dd, J=3.5, 0.8 Hz, 1 H), 7.50 (dd, J=1.8, 0.8 Hz, 1 H); $^{13}$C NMR (CDCl$_3$, –50° C.) δ 43.3 (t), 45.7 (t), 46.3 (t), 47.7 (t), 111.4 (d), 116.4 (d), 144.2 (d), 146.8 (s), 159.2 (s)

Example 4

The preparation of N-(3-trimethylsiloxybutylcarbonyl) piperazine (Compound 6)

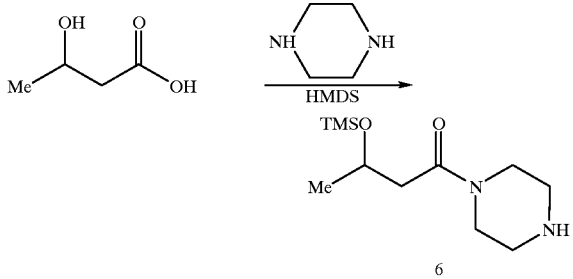

The procedures of Example 1 were followed except that 3-hydroxylbutric acid (3.4 grain s, 33 mmole), piperazine (5.7 grams, 66 mmole) and 1,1, 1,3,3,3-hexamethyldisilazane (10.6 grams, 66 mmole) were reacted for 5 hours under 110° C. After extraction purification, 6.7 grams of Compound 6 was obtained. Yield: 83%.

Compound 6: $^1$H NMR (CDCl$_3$) δ 0.11 (s, 9 H), 1.24 (d, J=6.1 Hz, 3 H), 2.33 (dd, J=14.2, 5.2 Hz, 1 H), 2.64 (dd, J=14.2, 7.3 Hz, 1 H), 2.66 (br s, 1 H, NH), 2.86–2.91 (m, 4 H), 3.48–3.66 (m, 4 H), 4.33 (ddt, J=7.3, 6.1, 5.2 Hz, 1 H); $^{13}$C NMR (CDCl$_3$) 1.38, 24.26, 42.44, 42.67, 45.73, 46.05, 47.15, 66.61, 169.85

Example 5

The preparation of N-methyl-N-tetrahydrofuran-2-carbonyl trimethylene diamine (Compound 7)

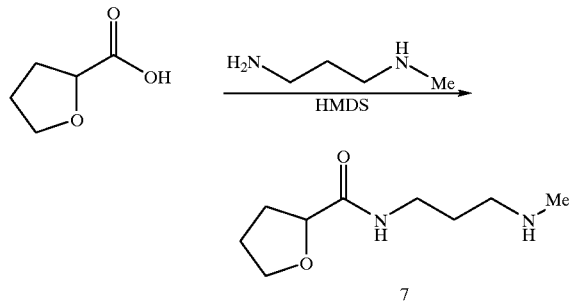

The procedures of Example 1 were followed except that tetrahydrofuran-2-carboxylic acid (3.7 grains, 30 mmole), N-methyl triethylene diamine (5.3 grams, 60 mmole) and 1,1,1,3,3,3-hexamethyldisilazane (9.7 grams, 60 mmole) were reacted for 5 hours under 110° C. After extraction purification, 4.7 grams of Compound 7 was obtained. Yield: 85%.

Compound 7: $^1$H NMR (CDCl$_3$) δ 1.63–1.68 (mn, 2 H), 1.73 (br s, 1 H, NH), 1.81–1.89 (mn, 2 H), 1.98–2.05 (mn, 1 H), 2.17–2.26 (m, 1 H), 2.39 (s, 3 H), 2.57–2.64 (m, 2 H), 3.26–3.34 (m;,2 H), 3.80–3.85 (m, 1 H), 3.86–3.91 (m, 1 H), 4.30 (dd, J=8.4, 5.7 Hz, 1 H), 7.22 (br s, 1 H, NH); $^{13}$C NMR (CDCl$_3$) δ 25.4 (t), 28.9 (t), 30.2 (t), 36.1 (q), 37.3 (t), 49.6 (t), 69.2 (t), 78.4 (d), 173.2 (s)

Example 6

The preparation of N-(thiophene-2-carbonyl) piperazine (Compound 8)

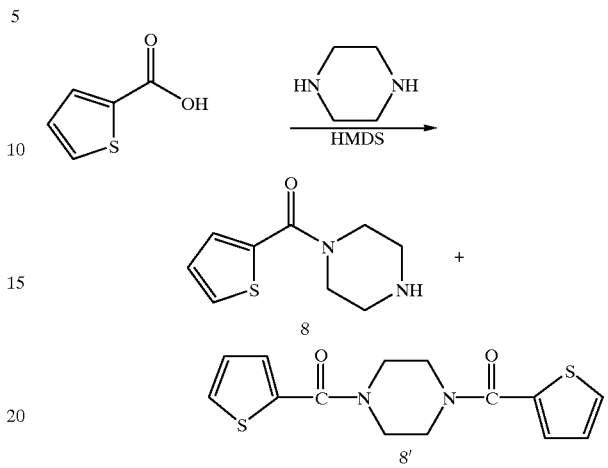

The procedures of Example 3 were followed except that thiophene-2-carboxylic acid (4.5 grams, 35 mmole), piperazine (6.0 grams, 70 mmole) and 1,1,1,3,3,3-hexamethyldisilazane (11.3 grams, 70 mmole) were reacted under 110° C. After extraction purification, 5.7 grams of Compound 8 (Yield: 72%) and 0.97 grams of diamide (Compound 8') were obtained.

Compound 8: $^1$H NMR (CDCl$_3$) δ 2.08 (s, 1 H, NH), 2.89–2.93 (m, 4 H), 3.70–3.74 (m, 4 H), 7.04 (dd, J=5.1, 3.7 Hz, 1 H), 7.28 (dd, J=3.7, 1.1 Hz, 1 H), 7.44 (dd, J=5.1, 1.1 Hz, 1 H); $^{13}$C NMR (CDCl$_3$–50° C.) δ 43.5 (t), 45.6 (t), 46.3 (t), 48.9 (t), 126.9 (d), 128.9 (d), 129.1 (d), 136.6 (s), 163.7 (s)

Example 7

The preparation of N-(2-tert-butoxycarbonyl-aminopropyl-carbonyl) piperazine (Compound 9)

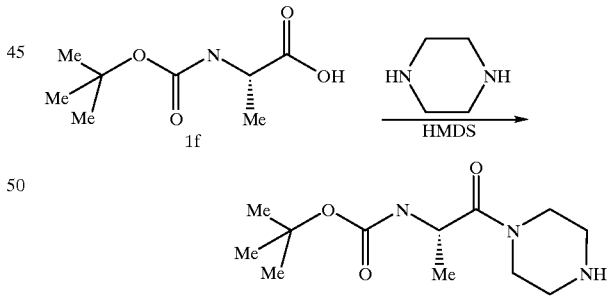

The procedures of Example 1 were followed except that Compound if (5.6 grams, 30 mmole), piperazine (5.2 grams, 60 mmole) and 1,1,1,3,3,3-hexamethyldisilazane (9.7 grams, 60 mmole) were reacted for 5 hours under 110° C. After extraction purification, 6.7 grams of Compound 9 was obtained. Yield: 87%.

Compound 9: a colorless solid, melting point 142.0–142.5° C., $^1$H NMR (CDCl$_3$) δ 1.27 (d, J=6.9 Hz, 3 H), 1.41 (s, 9 H), 2.10 (brs, 1 H, NH) 2.81–2.88 (m, 4 H) 3.40–3.43 (m, 1 H) 3.47–3.54 (m, 2 H), 3.58–3.61 (m, 1 H), 4.58 (dq, J=7.5, 6.9 Hz, 1 H), 5.59 (d, J=7.5 Hz, 1 H, amide NH); $^{13}$C NMR (CDCl$_3$) δ 19.36, 28.35, 42.84, 45.61, 45.99, 46.05, 46.33, 79.05, 155.07, 171.15

When the reaction conditions were changed to the temperature of 75° C. and the reaction time of 12 hours, after extraction purification, 3.9 grams of Compound 9 was obtained. Yield: 40%. After determination, the optical rotation was $[\alpha]_D^{23}$ –18.5°(c 0.2, MeOH). 91% of enantiomeric was retained.

Example 8

The preparation of N-(benzylcarbonyl)piperazine (Compound 10)

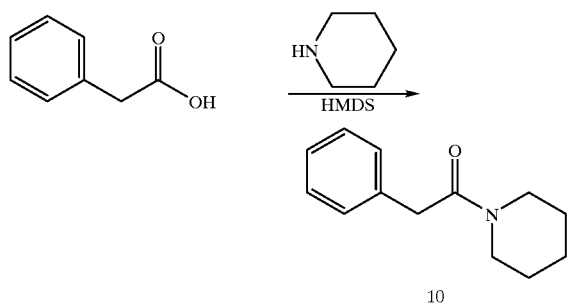

The procedures of Example 1 were followed except that phenyl acetic acid (3.4 grams, 25 mmole), piperazine (4.3 grams, 50 mmole) and 1,1,1,3,3,3-hexamethyldisilazane (4.0 grams, 25 mmole) were reacted for 5 hours under 110° C. After extraction purification, 4.2 grams of Compound 10 was obtained. Yield: 82%.

Compound 10 was transparent liquid: $^1$H NMR (CDCl$_3$) δ 1.33–1.37 (m, 2 H), 1.51–1.54 (m, 2 H) , 1.56–1.59 (m, 2 H) , 3.37 (t, J=5.5 Hz, 2 H), 3.58 (t, J=5.5 Hz, 2 H) , 3.73 (s, 2 H), 7.21–7.28 (m, 3 H), 7.29–7.33 (m, 2 H)

Example 9

The preparation of anti-hypertension medicines, Doxazosin

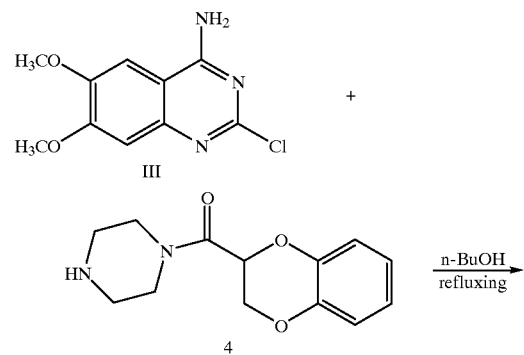

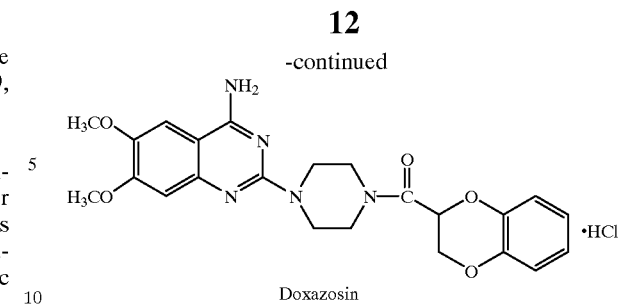

Doxazosin

4-Amino-2-chloro-6,7-bismethoxyquinazoline (III) (3.2 grams, 13.35 mmole), Compound 4 from Example 2 (3.4 grains, 13.75 mmole) and n-butanol (72 ml) were subjected to a 50 ml round-bottom flask and heated under refluxing for 3.5 hours under a nitrogen atmosphere. Cooling to 75° C., the solid products were filtered and collected, dried in an oven to obtain 5.25 grams of Doxazosin hydrochloride (10.76 mmole, Yield: 81%). The Doxazosin hydrochloride was added to a 1N NaOH solution and heated for dissolution. After cooling, the solution was extracted with 150 ml of dichloromethane twice. The organic layer was filtered and dried with anhydrous sulfate, and concentrated to obtain 4.61 grams of white Doxazosin solid: $^1$H NMR (CDCl$_3$) δ 3.63–4.09 (m, 8 H), 3.91 (s, 3H), 3.96 (s, 3H), 4.35 (dd, J=11.9, 7.9 Hz, 1H), 4.52 (dd, J=11.9, 2.4 Hz, 1H), 4.88 (dd, J=7.9, 2.4 Hz, 1H), 6.85–6.95 (m, 5H)

Example 10

The preparation of anti-hypertension medicines, Terazosin

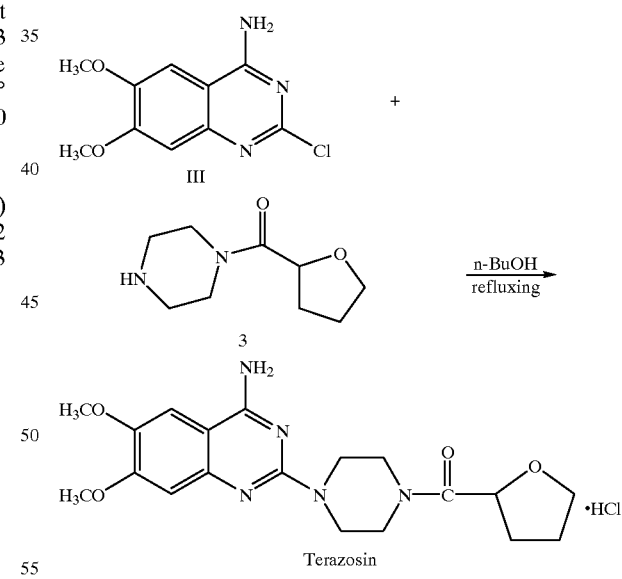

Terazosin

The procedures of Example 9 were followed except that Compound 3 from Example 1 (3.0 grams, 16.3 mmole) and 4-amino-2-chloro-6,7-bismethoxy quinazoline III (3.8 grams, 16.1 mmole) were reacted to obtain 5.0 grams of Terazosin hydrochloride (Yield: 73%). After alkalification, 4.7 grams of white Terazosin solid was obtained.

Comparative Example 1

The procedures of Example 1 were followed except that tetrahydrofuran-2-carboxylic acid (0.9 grams, 5 mmole), piperazine (0.86 grams, 10 mmole) and chlorotrimethylsilane (0.54 grams, 5 mmole) were reacted for 5 hours under 110° C. The reaction product was solid. No desired amide products were obtained after analysis.

As various changes could be made in the above processes without departing from the scope of the present invention, it is intended that the above-described specific working examples be interpreted as illustrative and not in a limiting sense.

What is claimed is:

1. A process for the preparation of amides, comprising reacting amines with carboxylic acids in the presence of silicon amines.

2. The process of claim 1, wherein the amines have the following formulae:

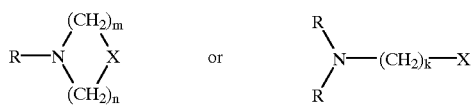

wherein R is the same or different and selected from hydrogen, $C_{1-6}$ alkyl, and $C_{2-6}$ alkenyl; X is CR or NR, R is as defined above; m is 2 or 3; n is 2 or 3; and k is 1 to 8.

3. The process of claim 1, wherein the carboxylic acids have the following formula:

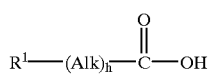

wherein $R^1$ is selected from hydrogen, $C_{1-6}$ alkyl, $C_{1-6}$ alkoxy, $C_{2-6}$ alkenyl, aryl, saturated, partially saturated or unsaturated heterocyclyl containing from 4 to 7 ring members and from 1 to 3 heteroatoms each independently selected from the group consisting of nitrogen, oxygen and sulfur, the heterocyclyl being optionally fused with another such heterocyclyl ring or phenyl, and

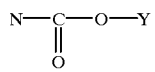

wherein Y is selected from hydrogen, $C_{1-6}$ alkyl, and $C_{2-6}$ alkenyl; Alk is unsubstituted or substituted alkylene; and h is 0 to 4.

4. The process of claim 1, wherein the silicon amines have the following formula:

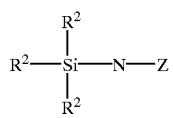

wherein $R^2$ is the same or different and selected from hydrogen, $C_{1-6}$ alkyl, and $C_{2-6}$ alkenyl; Z is selected from hydrogen, $C_{1-6}$ alkyl, $C_{2-6}$ alkenyl, and silyl.

5. The process of claim 2, wherein R is selected from hydrogen and $C_{1-6}$ alkyl.

6. The process of claim 2, wherein R is selected from hydrogen and methyl; m is 2; n is 2 and/or k is 3.

7. The process of claim 3, wherein $R^1$ is selected from $C_{1-6}$ alkyl, phenyl, 4 to 7 membered heterocyclyl which contains 1 to 3 the same or different hetero atoms selected from nitrogen, oxygen and sulfur, and optionally fused with phenyl or heterocyclyl, and

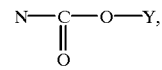

wherein Y is straight or branch $C_{1-6}$ alkyl.

8. The process of claim 3, wherein Alk is unsubstituted, hydroxyl-substituted, or methyl-substituted alkylene; and/or h is 0 to 2.

9. The process of claim 4, wherein $R_2$ is unsubstituted $C_{1-6}$ alkyl, and/or Z is $C_{1-6}$ alkyl-substituted silyl.

10. The process of claim 4, wherein the silicon amine is 1,1,1,3,3,3-hexamethyldisilazane.

11. A process for the preparation of quinazoline derivatives, comprising reacting amines with carboxylic acids in the presence of silicon amines to obtain amides, and contacting the resulting amides with a quinazoline of the following formula:

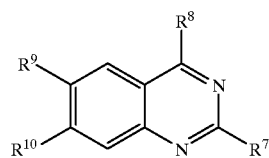

wherein $R^7$, $R^8$, $R^9$ and $R_{10}$ are independently selected from halogen, hydrogen, amino, $C_{1-8}$ alkyl, $C_{2-8}$ alkenyl, $C_{3-8}$ cycloalkyl, $C_{3-8}$ cycloalkenyl, $C_{6-12}$ aryl, $C_{1-8}$ alkoxy, $C_{1-8}$ alkylthio and $C_{3-8}$ heterocyclyl.

12. The process of claim 11, wherein the amines have the following formula:

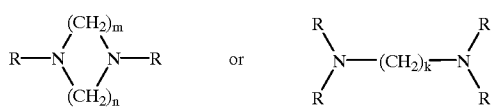

wherein R is the same or different and selected from hydrogen, $C_{1-6}$ alkyl, and $C_{2-6}$ alkenyl; m is 2 or 3; n is 2 or 3; and k is 1 to 8.

13. The process of claim 11, wherein the carboxylic acids have the following formula:

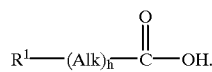

wherein $R^1$ is selected from hydrogen, $C_{1-6}$ alkyl, $C_{1-6}$ alkoxy, $C_{2-6}$ alkenyl, aryl, heterocyclyl, and

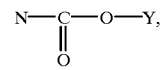

wherein Y is selected from hydrogen, $C_{1-6}$ alkyl, and $C_{2-6}$ alkenyl; Alk is unsubstituted or substituted alkylene; and h is 0 to 4.

14. The process of claim 11, wherein the silicon amines have the following formula:

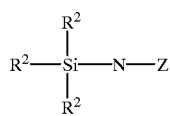

wherein $R^2$ is the same or different and selected from hydrogen, $C_{1-6}$ alkyl, and $C_{2-6}$ alkenyl; Z is selected from hydrogen, $C_{1-6}$ alkyl, $C_{2-6}$ alkenyl, and silyl.

15. The process of claim 12, wherein R is selected from hydrogen and $C_{1-6}$ alkyl.

16. The process of claim 12, wherein R is selected from hydrogen and methyl; m is 2; n is 2; and/or k is 3.

17. The process of claim 13, wherein $R^1$ is selected from $C_{1-6}$ alkyl, phenyl, 4 to 7 membered heterocyclyl which contains 1 to 3 the same or different hetero atoms selected from nitrogen, oxygen and sulfur, and optionally fused with phenyl or heterocyclyl, and

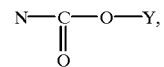

wherein Y is straight or branch $C_{1-6}$ alkyl.

18. The process of claim 13, wherein Alk is unsubstituted, hydroxyl-substituted, or methyl-substituted alkylene; and/or h is 0 to 2.

19. The process of claim 14, wherein $R^2$ is unsubstituted $C_{1-6}$ alkyl ; and/or Z is $C_{1-6}$ alkyl-substituted silyl.

20. The process of claim 14, wherein the silicon amine is 1,1,1,3,3,3-hexamethyldisilazane.

* * * * *

UNITED STATES PATENT AND TRADEMARK OFFICE
CERTIFICATE OF CORRECTION

PATENT NO.    : 6,313,293 B1
DATED         : November 6, 2001
INVENTOR(S)   : Chou et al.

It is certified that error appears in the above-identified patent and that said Letters Patent is hereby corrected as shown below:

Column 10,
Line 66, before "2.81-2.88" insert -- , --;
Line 66, after "(m, 4 H)" insert -- , --;
Line 67, before "3.47-3.54" insert -- , --;

Column 12,
Line 15, change "grains" to -- grams --;

Column 13,
Line 12, after "reacting" insert -- primary or secondary amines --

Column 14,
Line 13, change "$R_2$" to -- $R^2$ --; and
Line 32, change "$R_{10}$" to -- $R^{10}$ --.

Signed and Sealed this

Thirteenth Day of August, 2002

*Attest:*

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO.   : 6,313,293 B1
DATED        : November 6, 2001
INVENTOR(S)  : Chou et al.

It is certified that error appears in the above-identified patent and that said Letters Patent is hereby corrected as shown below:

Column 1,
Line 66, change "N-acylalkylenediarnine" to -- N-acylalkylenediamine --;

Column 2,
Line 19, change "carbodumides" to -- carbodiimides --;
Line 24, change "N-acylalkylenediarnine" to -- N-acylalkylenediamine --;

Column 4,
Line 15, change "brormide" to -- bromide --;

Column 7,
Line 59, change "pierazine" to -- piperazine --;

Column 9,
Line 24, change "3-hydroxylbutric" to -- 3-hydroxylbutyric --;
Line 56, change "triethylene" to -- trimethylene --;
Line 62, after "1.81-1.89" change "(mn, 2 H)" to -- (m, 2 H) --;
Line 62, after "1.98-2.05" change "(mn, 1 H)" to -- (m, 1 H) --;

Column 10,
Line 59, after "Compound" change "if" to -- 1f --.

Signed and Sealed this

Thirteenth Day of May, 2003

JAMES E. ROGAN
*Director of the United States Patent and Trademark Office*